United States Patent
Gohmann

(10) Patent No.: US 9,845,073 B2
(45) Date of Patent: Dec. 19, 2017

(54) SENSOR DEVICE FOR RECORDING MOISTURE ON A WINDOW AND MOTOR VEHICLE

(71) Applicant: Hella KGaA Hueck & Co., Lippstadt (DE)

(72) Inventor: Alexander Gohmann, Bremen (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 0 days.

(21) Appl. No.: 15/193,795

(22) Filed: Jun. 27, 2016

(65) Prior Publication Data

US 2016/0375864 A1     Dec. 29, 2016

(30) Foreign Application Priority Data

Jun. 29, 2015   (DE) ......................... 10 2015 008 298

(51) Int. Cl.
| | | |
|---|---|---|
| *G01N 21/41* | (2006.01) | |
| *B60S 1/08* | (2006.01) | |
| *G01N 21/552* | (2014.01) | |

(52) U.S. Cl.
CPC ........ *B60S 1/0837* (2013.01); *G01N 21/4133* (2013.01); *G01N 21/552* (2013.01)

(58) Field of Classification Search
CPC .. G01N 21/41; G01N 21/4133; G01N 21/431; G01N 21/43; G01N 21/552
USPC ......................................................... 356/128
See application file for complete search history.

(56) References Cited

U.S. PATENT DOCUMENTS

| | | | |
|---|---|---|---|
| 4,936,657 A | 6/1990 | Tejima et al. | |
| 5,391,891 A | 2/1995 | Weigleb et al. | |
| 5,661,303 A | 8/1997 | Teder | |
| 8,082,783 B2 | 12/2011 | Backes | |
| 8,269,202 B2 | 9/2012 | Backes | |
| 2006/0043322 A1* | 3/2006 | Ishikawa ............... | B60S 1/0822 250/573 |
| 2008/0297803 A1* | 12/2008 | Backes ................ | B60S 1/0822 356/445 |
| 2009/0284735 A1* | 11/2009 | Backers ................... | G01J 1/04 356/73 |
| 2010/0147067 A1* | 6/2010 | Backes ............... | G01N 21/552 73/170.17 |

(Continued)

FOREIGN PATENT DOCUMENTS

| | | |
|---|---|---|
| DE | 3624188 A1 | 2/1987 |
| DE | 4006174 C1 | 7/1991 |

(Continued)

*Primary Examiner* — Tarifur Chowdhury
*Assistant Examiner* — Md M Rahman
(74) *Attorney, Agent, or Firm* — Muncy, Geissler, Olds & Lowe, P.C.

(57) ABSTRACT

With a sensor device for recording moisture on a window pane with a transmitter and a receiver and an optical unit arranged between the transmitter and the receiver, wherein the optical unit includes an optical input unit facing the transmitter, an optical output unit facing the receiver and a coupling-in and coupling-out region on the side of the window pane, the coupling-in and coupling-out region is optically separated from the optical input unit and the optical output unit such that the electromagnetic waves emitted by the transmitter are refracted. A particularly compact constructional design is achieved thereby.

8 Claims, 1 Drawing Sheet

(56) References Cited

U.S. PATENT DOCUMENTS

2014/0353474 A1   12/2014   Niemann et al.

FOREIGN PATENT DOCUMENTS

| DE | 19830120 A1 | 2/1999 |
| DE | 69714547 T2 | 3/2003 |
| DE | 102008020171 A1 | 10/2009 |
| DE | 102008061616 A1 | 6/2010 |
| DE | 10201300926 A1 | 12/2014 |

* cited by examiner

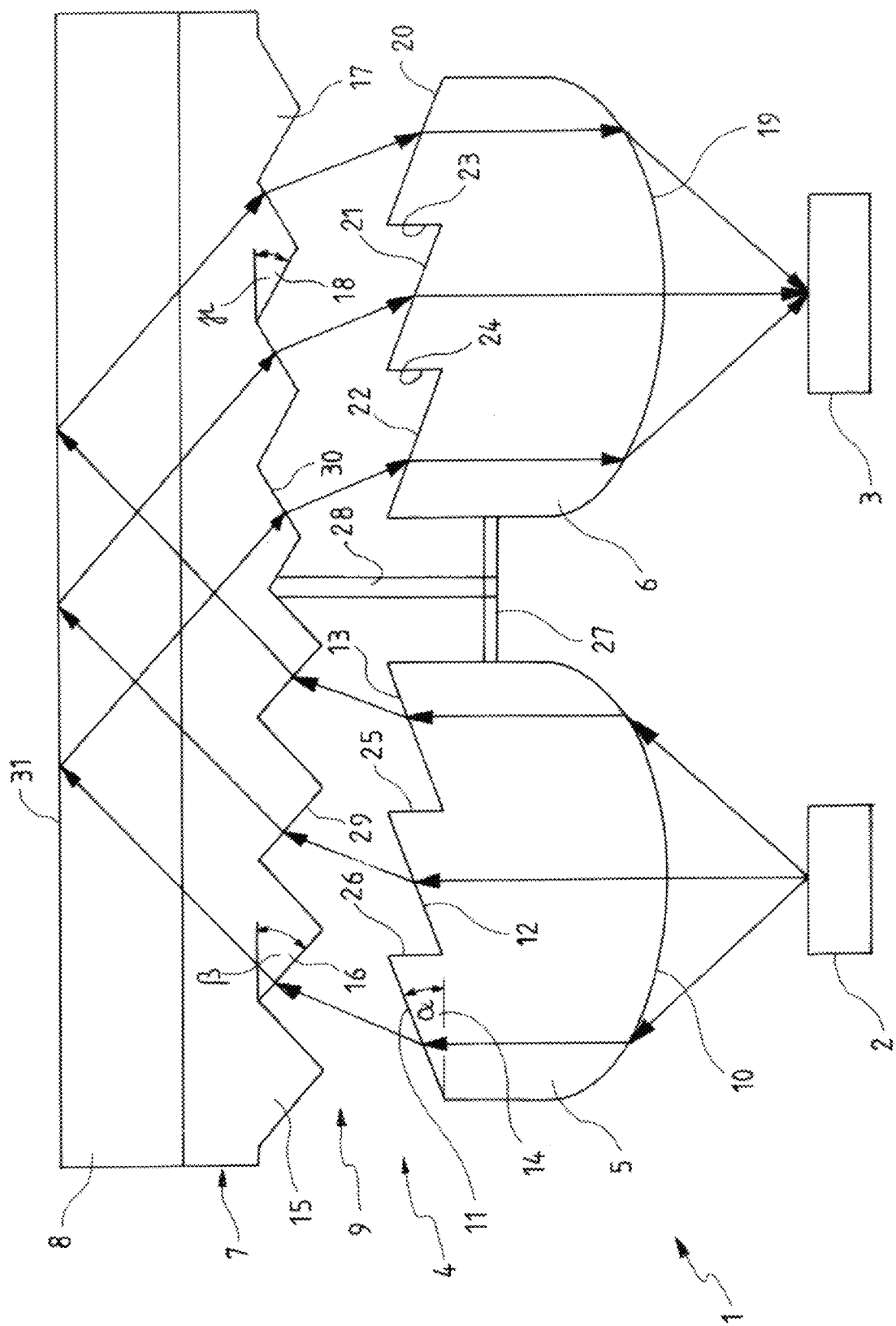

SENSOR DEVICE FOR RECORDING MOISTURE ON A WINDOW AND MOTOR VEHICLE

BACKGROUND OF THE INVENTION

Field of the Invention

The invention relates to a sensor device for recording moisture on a window, with a transmitter and a receiver and with an optical unit arranged between the transmitter and the receiver, wherein the optical unit comprises an optical input unit facing the transmitter, an optical output unit facing the receiver and a coupling-in and coupling-out region on the side of the window pane.

Brief Description of the Related Art

Such sensor devices serve to record moisture on window panes, in particular on windscreens of motor vehicles. They are used to ascertain, whether drops or water are present on the window pane, and then to control a windscreen wiper on the basis of this information. Headlight control is also feasible.

A generic sensor device is known from the DE 40 06 174 C1. The windscreen has an optical unit arranged on it, where radiation, in particular light, is emitted from a transmitter into the optical unit at one end. The radiation is reflected a number of times in the optical unit and in the window pane in contact with the surface of the optical unit. Depending on the degree of wetting of the window pane, the rays are coupled out of the pane. The other end of the optics has a receiver arranged on it, which supplies a signal inversely proportional to the amount of precipitation. The sensor device operates according to the optical principle of total reflection. A further similar sensor device is known from the DE 10 2013 009 126 A1.

SUMMARY OF THE INVENTION

The invention is based on the requirement to propose a sensor device of the kind mentioned in the beginning, which requires very little constructional space.

This requirement is met by a sensor device with the characteristics of patent claim 1 and with a motor vehicle with the characteristics of patent claim 8. Advantageous developments of the invention are cited in the sub-claims.

With a sensor device for recording moisture on a window pane with a transmitter and a receiver and an optical unit arranged between the transmitter and the receiver, wherein the optical unit comprises an optical input unit facing the transmitter, an optical output unit facing the receiver and a coupling-in and coupling-out region on the side of the window pane, provision is made according to the invention for an air gap between the coupling-in and coupling-out region, for the coupling-in and coupling-out region to be optically separated from the optical input unit or the optical output unit in such a way that the electromagnetic waves emitted by the transmitter are refracted, for the coupling-in and coupling-out region to comprise a geometry different from the optical input unit, for the side of the optical input unit facing the coupling-in and coupling-out region to comprise a number of ramps rising in direction of the receiver when seen in cross-section, for the coupling-in and coupling-out region to comprise a surface structure triangular in cross-section, and for each ramp of the optical input unit to have associated with it a triangular structure of the coupling-in and coupling-out region.

According to the invention the whole optics is divided into several regions, so that the electromagnetic waves undergo refraction within the optics. As a result the geometry of guiding the light can be advantageously influenced making it possible to construct a particularly compact sensor device, in which the electromagnetic waves emitted by the transmitter are simultaneously utilised in an optimal manner, enabling the capacity of the receiver to be exploited and correspondingly distinguishable intensities to be received by the receiver. Preferably the transmitter is an LED, i.e. a light-emitting diode and the receiver is preferably a photo diode.

Preferably it is not just the optical input unit or the optical output unit which is optically separated from the coupling-in and coupling-out region, but preferably both the optical input unit and the optical output unit are optically separated from the coupling-in and coupling-out region, so that in the sensor device refraction takes place at least twice within the beam path, i.e. one time between the optical input unit and the coupling-in and coupling-out region and then for a second time between the coupling-in and coupling-out region and the optical output unit. Specifically there are in fact four refraction operations, because a first refraction takes place respectively at the transition between optical input/output unit and intermediate medium and a second refraction takes place at the transition between intermediate medium and coupling-in and coupling-out region. It is particularly convenient, if an air gap is present between the coupling-in and coupling-out region and the optical input unit and/or the optical output unit resulting respectively, in refraction (in fact in two refractions).

The optical units preferably consist of glass or a transparent plastic with a corresponding refraction index. At the transition into air a refraction takes place not only during the exit from the optical input unit into the air gap but also during transition from the air gap into the coupling-in and coupling-out region. In the same way a refraction takes place during the exit from the coupling-in and coupling-out region into the air gap and a renewed refraction at re-entry from the air gap into the optical output unit. It is also feasible to construct the optical unit from different materials, i.e. to provide, instead of the air gap, a plastic or a different material with a different refraction index, so that a refraction takes place between the optical input unit from a first plastic material and the second material with a refraction index different therefrom.

The optical input unit preferably comprises a focussing surface on the side of the transmitter. Preferably the transmitter, in particular a LED, is arranged centrally and symmetrically to the transmitter-side surface and the surface is configured in a corresponding manner, i.e. symmetrically and convex. The optical input unit is preferably essentially aligned vertically to the coupling-in and coupling-out region and thus also, in particular, to the window pane behind it. This vertical alignment of the optical input unit and the LED behind it relative to the coupling-in and coupling-out region, is made possible because of the separation of optical input unit and coupling-in and coupling-out region and the refraction of the rays taking place in the process thereof. In summary this results in a reduced constructional space requirement for the sensor device.

According to the invention the optical input unit, on its side facing the coupling-in and coupling-out region, comprises a number of ramps rising in direction of the receiver when seen in cross-section. This leads to a refraction of the rays for a corresponding refraction index of the separating material, in particular air, to a targeted refraction. Conveniently, the ramps, in relation to the horizontal, comprise an angle of approx. 38°+−10° and preferably +−5°.

According to the invention the coupling-in and coupling-out region comprises a surface structure which is triangular in cross-section. This is dimensioned and positioned such that each ramp of the optical input unit is associated with a triangular structure of the coupling-in and coupling-out region. In particular, this is positioned such that the electromagnetic waves, which are refracted at a ramp, are incident upon one side of the triangle, wherein the side of the triangle is that side which when seen in direction from the base to the tip, points in direction of the receiver/the coupling-out region. The triangular structure has an angle of 50° in relation to the horizontal and to this end has a deviation of +−10°, preferably +−5°.

Preferably the optical input unit comprises between two and five ramps. In this range the design is particularly meaningful. Theoretically and dependent on the production possibilities however, other designs are possible, i.e. optical input units with a multitude of ramps which are then correspondingly smaller. A merely obliquely rising surface would also be feasible, but this would then require a larger distance of the optical input unit from the coupling-in and coupling-out region. Preferably the ramps and the triangular structure have flat surfaces. But it may also be convenient to design concave or convex surfaces in order to cater for a further variable for directing the beam path.

The above statements for the optical input unit analogously also apply to the optical output unit. The optical output unit preferably comprises a number of ramps rising in direction of the transmitter/the optical output unit, when seen in cross-section. The ramps of the optical input unit and the optical output unit preferably comprise identical dimensions. Only the direction of the ramps is different, i.e. they point in opposite directions. Preferably the optical output unit also comprises a focussing surface which faces the receiver. The optical input unit and the optical input unit are preferably configured mirror-symmetrically as regards an imaginary vertical between optical input unit and optical output unit. The coupling-in and coupling-out region opposite to the optical output unit also comprises a triangular surface structure when seen in cross-section. The angles of the triangular surface structure in the area of the optical output unit are conveniently different from the angles of the coupling-in and coupling-out region of the triangular surface structure in the area of the optical input unit. Here the angle relative to the horizontal is preferably 30°+−10°, preferably +−5°.

Alternatively it is possible to have same size angles for both the coupling-in region and the coupling-out region.

The height of the ramps and the height of the triangular surface structure of the coupling-in and coupling-out region are of approximately the same magnitude and are preferably different by a factor of maximum two.

In another preferred embodiment of the invention the optical input unit and the optical output unit are mechanically connected with each other. As a result their position in relation to each other is fixed. Production and adjustment tolerances can thus be minimised. Preferably the optical input unit and the optical output unit are also connected mechanically to the coupling-in and coupling-out region. To this end connecting struts are preferably provided. If optical reflection does not take place in an air gap but with a plastic with corresponding refraction index, the connection between optical input unit, optical output unit and coupling-in and coupling-out region is already existent and adjustment thereby ensured.

Another aspect of the invention consists in providing a motor vehicle with a window pane, in particular a windscreen and an above-described sensor device.

BRIEF DESCRIPTION OF THE DRAWING

The invention will now be described with reference to the exemplary embodiment shown in the FIGURE. The sole FIGURE of the drawing shows, in a schematically drawn view, a cross-section through a sensor device on a window pane.

DETAILED DESCRIPTION OF THE PREFERRED EMBODIMENTS

The FIGURE shows a sensor device 1. The sensor device 1 comprises a transmitter 2, here a LED, a receiver 3, here a photo diode, and an optical unit 4. The optical unit 4 is composed of an optical input unit 5, a coupling-in and coupling-out region 7 and an optical output unit 6. The sensor device 1 with the coupling-in and coupling-out region 7 is arranged flat and flush with a window pane 8, in particular a windscreen of a motor vehicle.

The principle mode of operation is such that electromagnetic waves, in particular light emitted by the transmitter 2, are received and bunched by the optical input unit 5, and then, from the optical input unit, reach the coupling-in and coupling-out region 7 and thus the window pane 8. Care must be taken that the electromagnetic waves are incident upon the pane 8, in particular the outside 31 of the pane, under such an angle that they hit the pane flat such that total reflection is obtained. The totally reflected electromagnetic waves get into the optical output unit 6 via the coupling-in and coupling-out region 7 and from there into the receiver 3. If, however, water drops are present on the window pane 8, some of the electromagnetic waves are coupled out and the proportion of light or of the totally reflected electromagnetic waves becomes less and the intensity measured at the receiver 3 is reduced accordingly.

The transmitter 2 is arranged below the optical input unit 5. In relation to the pane 8 the transmitter 2 and the optical input unit 5 are arranged below the pane 8 and vertically aligned therewith. The optical input unit 5 comprises a focussing surface 10 directed towards the transmitter 2, wherein the surface 10 is aligned and designed such that the electromagnetic waves emitted by the transmitter 2 progress in parallel to each other and vertically to the pane 8 within the optical input unit 5. Exiting of the electromagnetic waves from the optical input unit 5 takes place on the side of the optical input unit 5 which faces the pane. Here a number of ramps 11, 12, 132 are arranged, or in other words, form the surface. The ramps 11, 12, 13 comprise an angle α relative to the horizontal, which here is marked with 14 and which is approx. 38°. Certain variations and deviations are of course possible here. Between the ramp 11 and the ramp 12 there exists a ramp edge 26, which is vertically aligned with regard to the pane 8. The ramps 11, 12, 13 in the FIGURE rise from left to right. The rise therefore is aligned in direction of the beam path, i.e. also in direction of the receiver 3. The electromagnetic waves then pass through the ramps, are refracted in there because an air gap 9 has been provided between the optical input unit 5 and the coupling-in and coupling-out region 7, so that between the optical input unit 5 and the air gap 9 an optical interface exists, at which a refraction takes place. Upon re-entry into the optical unit, i.e. from the air gap 9 into the coupling-in and coupling-out region 7, there is another optical interface resulting in a renewed refraction. The coupling-in and coupling-out region 7 comprises a triangular structure 15, wherein this is aligned and dimensioned such that each ramp 11, 12, 13 is associated with an active side 29 of the triangular structure 15 in the coupling-in region. The active sides 21, with regard to a horizontal, have an angle γ of approx. 45°. This is the side which seen from the base to the tip is aligned in direction of the receiver 3. The number of ramps 11, 12, 13 and of the actives sides of the triangular structure 15 correspond to each other. Preferably the number of ramps and thus also of the triangular structure in the input region is from two to five. This is a good compromise with regard to the achievable height and possibility of production. In principle, however, almost any other numbers are possible. For a suitably small design up to 100 ramps may be provided. The electromagnetic waves then pass through the coupling-in and coupling-out region 7 and are reflected by the pane 8. The coupling-in and coupling-out region 7 simultaneously forms the sensor housing and is, of course, designed so as to be transparent for the electromagnetic waves. The electromagnetic waves are reflected on the outside 31 of the pane and are then incident upon the triangular structure 17 in the coupling-out region. The triangular structure 17 in the coupling-out region is designed with an angle γ of 30° to the horizontal. The active side 30 of the triangular structure 17 in the coupling-out region is that side, which seen from the base to the tip is aligned in direction of the transmitter 2. This is the side upon which the electromagnetic waves reflected at the outside 31 of the pane are incident, they are then refracted during transition into the other medium, here realised by the air gap 9, and after passing through the air gap 9 hit the optical input unit 6, at which renewed refraction takes place at the optical interface. The optical output unit 6 here is designed with ramps 20, 21, 22, which are configured so as to rise in direction of the transmitter 2/the coupling-in region. In other respects the optical output unit 6 corresponds to the optical input unit 5 and is designed in a mirror-symmetrical manner thereto. The triangular structure 17 in the coupling-out region and the ramps 20, 21, 22 of the optical output unit 6 are selected and arranged such that the electromagnetic waves within the optical output unit 6 progress in parallel to each other and at right angles to the coupling-in and coupling-out region 7, in particular in relation to the pane 8. The triangular structure 17 of the coupling-out region is designed and dimensioned such that each active side 30 of the triangular structure is precisely associated with a ramp 20, 21, 22, so that the beam path progresses through an active side 30 to an associated ramp 20, 21, 22 of the optical output unit 6. The electromagnetic waves progressing in parallel through the optical output unit 6 are focussed via a focussing surface 11 onto the receiver 3, realised here as a photo diode. This ensures that the beam power which is input, is fully utilised and that intensity measuring is optimal.

The optical input unit 5 and the optical output unit 6 are mechanically connected with each other via a connecting strut 27. Furthermore provision is made for a connecting strut 28 to the coupling-in and coupling-out region 7. Naturally further and additional connecting struts or other mechanical connections can be used, with which an exact alignment and adjustment of the optical units relative to each other is possible. Since the alignment of the optical input unit 5 relative to the coupling-in and coupling-out region 7, in particular to the triangular structure 15 of the coupling-in region and the alignment of the triangular structure 17 of the coupling-out region to the optical output unit 6 is crucial, such a mechanical connection is preferred.

All features mentioned in the above description and in the claims can be randomly and selectively combined with the features of the independent claim. The disclosure of the invention is therefore not limited to the described or claimed feature combinations, rather all feature combinations meaningful in terms of the invention are considered to have been disclosed.

The invention claimed is:

1. A sensor device for recording moisture on a window pane with a transmitter and a receiver and an optical unit arranged between the transmitter and the receiver, wherein the optical unit comprises an optical input unit facing the transmitter, an optical output unit facing the receiver and a coupling-in and coupling-out region on the side of the window pane, wherein:
   an air gap is arranged between the coupling-in and coupling-out region;
   the coupling-in and coupling-out region is optically separated from the optical input unit and the optical output unit in such a way that the electromagnetic waves emitted by the transmitter are refracted;
   the coupling-in and coupling-out region comprises a geometry different from the optical input unit;
   the side of the optical input unit facing the coupling-in and coupling-out region comprises a number of ramps rising in direction of the receiver when seen in cross-section;
   the coupling-in and coupling-out region comprises a surface structure triangular in cross-section; and
   each ramp of the optical input unit has a triangular structure of the coupling-in and coupling-out region associated with it.

2. The sensor device according to claim 1, wherein the coupling-in and coupling-out region is optically separated from both the optical input unit and the optical output unit.

3. The sensor device according to claim 1, wherein the optical input unit comprises a focussing surface on the transmitter side.

4. The sensor device according to claim 1, wherein the optical input unit is essentially vertically aligned with respect to the coupling-in and coupling-out region.

5. The sensor device according to claim 1, wherein the optical input unit comprises between two and five ramps.

6. The sensor device according to claim 1, wherein the height of the ramps and the height of the triangular surface structures are different from each other by a factor of maximum two.

7. The sensor device according to claim 1, wherein the optical input unit are mechanically connected with each other.

8. A motor vehicle with a window pane and a sensor device arranged thereon according to claim 1.

* * * * *